United States Patent [19]

Gonser

[11] 4,112,335
[45] Sep. 5, 1978

[54] RAPID PULSE ULTRAVIOLET LIGHT APPARATUS

[75] Inventor: Donald I. Gonser, York, Pa.

[73] Assignee: Dentsply Research & Development Corp., Milford, Del.

[21] Appl. No.: 806,316

[22] Filed: Jun. 13, 1977

Related U.S. Application Data

[63] Continuation of Ser. No. 560,290, Mar. 20, 1975, abandoned.

[51] Int. Cl.$^2$ .......................................... H05B 37/00
[52] U.S. Cl. .............................. 315/241 R; 313/184; 313/224
[58] Field of Search ................ 313/184, 198, 224; 315/241 R; 350/96.1

[56] References Cited

U.S. PATENT DOCUMENTS

| | | | |
|---|---|---|---|
| 2,261,215 | 11/1941 | Bird | 250/504 |
| 2,977,508 | 3/1961 | Germeshausen | 313/196 X |
| 3,218,510 | 11/1965 | Schulz | 313/197 X |
| 3,350,602 | 10/1967 | Germeshausen et al. | 313/196 X |
| 3,712,984 | 1/1973 | Lienhard | 350/96 R X |
| 3,868,513 | 2/1975 | Gonser | 250/504 |

*Primary Examiner*—Lawrence J. Dahl
*Attorney, Agent, or Firm*—Albert W. Preston, Jr.

[57] ABSTRACT

An ultraviolet lamp is disclosed wherein the light source is a rapid pulse unconfined xenon arc tube containing more than three atmospheres of xenon gas pressure, and providing an output limited to wavelengths greater than 320 nanometers. Associated circuitry for operating the tube and associated light transmitting means for utilizing the output of the tube are also disclosed.

14 Claims, 6 Drawing Figures

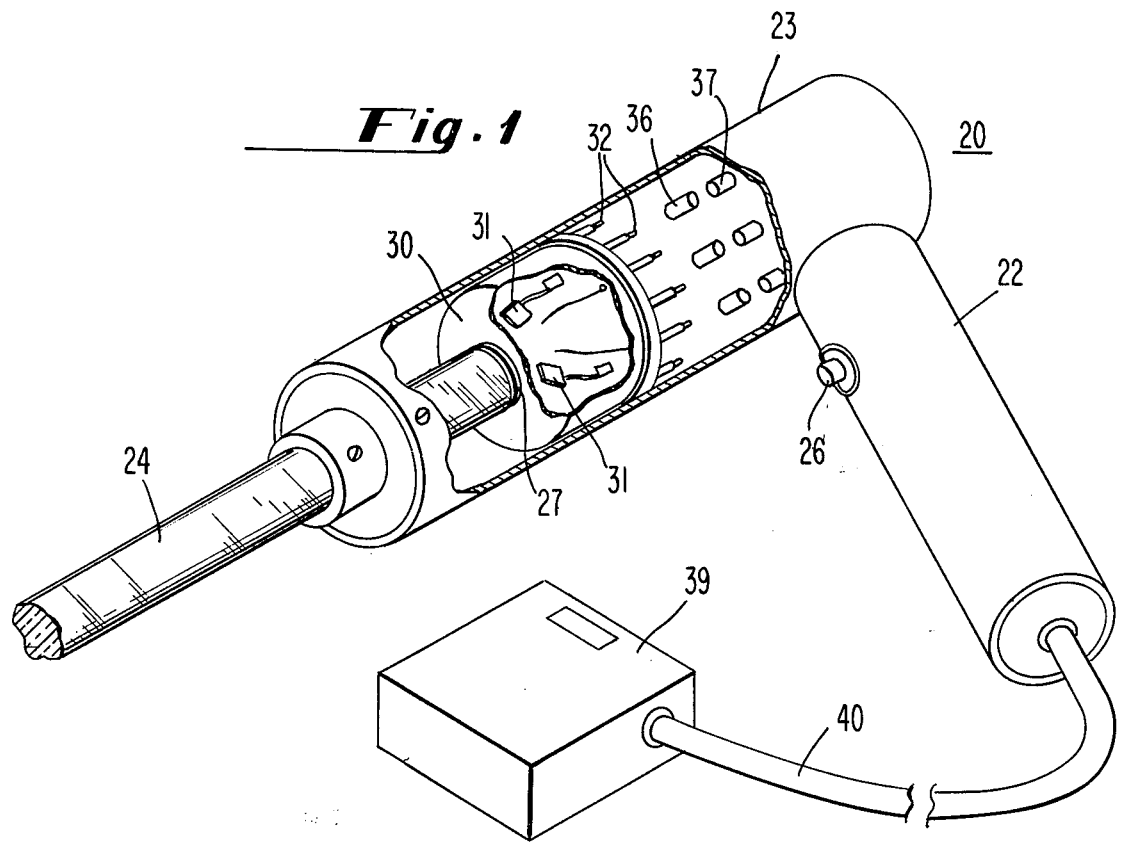
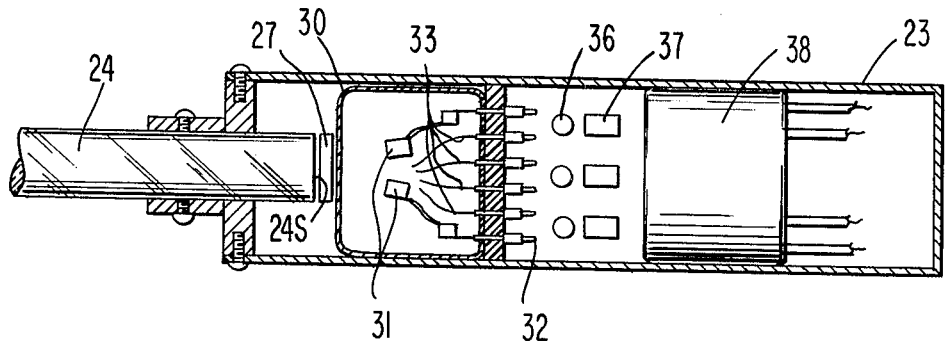

RAPID PULSE ULTRAVIOLET LIGHT APPARATUS

REFERENCE TO RELATED APPLICATION

This application is a continuation of application Ser. No. 560,290, filed Mar. 20, 1975, now abandoned. Any portions of such application not included herein are incorporated by reference.

BACKGROUND OF THE INVENTION

This invention adds to the field of pulsed discharge light sources and, more particularly, pulsed light sources which are efficient in delivering light energy in the ultraviolet range of the electromagnetic spectrum and are capable of being adapted to deliver ultraviolet light energy to a small area.

DESCRIPTION OF THE PRIOR ART

In the fields of medicine and dentistry there have been recent developments which have increased the interest in and use of ultraviolet light energy both as a treatment agent as well as for its ability to be used to activate the polymerization of certain kinds of polymeric compositions to produce splints, dental sealants, dental filling materials and dental adhesives for orthodontic appliances and the like. In particular, in the protection of the teeth of human beings, and especially children, an important development in decreasing the incidence of cavities involves the technique of applying a liquid resin which penetrates crevices in the occlusal or biting surfaces of teeth, and which can be polymerized to form a tough adherent coating. Ultraviolet radiation has been used extensively as one mechanism for activating that resin polymerization. Other applications for ultraviolet activation of resin polymerization are for tooth filling materials for tooth restoration, cements for orthodontic attachments and polymerization techniques for crown and bridge prosthesis.

Ultraviolet lamps currently available for providing ultraviolet light radiation for the activation and curing of polymerizable liquid coatings or sealants and the like have generally been most suitable for techniques not requiring great penetration of the polymerizable mass of material. To be suitable for such applications an ultraviolet light would have to be sufficiently rich in those wave lengths which are most efficient for the curing of the polymer in question. Otherwise, it would be subject to the disadvantage of having to be handheld for too long a period of time thereby inducing both patient and operator discomfort. Likewise, ultraviolet light devices currently available in the art might be prone to building up an uncomfortable amount of heat if they were required to cure material to a sufficient depth that the device was required to be on longer than a normally tolerable period of time.

The basic cause of course for any excessive heating which might occur in prior art devices derives from the fact that they were relatively insufficient in producing emissions at the desired ultraviolet wave lengths for the polymerization of the materials being used, i.e., approximately between 320 nanometers and 390 nanometers. In addition, the devices currently in use require a long warm-up time thereby tending to reach a high threshold temperature while not in use thereby diminishing the useful working life. Additionally, prior art devices have been characterized by undesirably high total ultraviolet light output flux.

SUMMARY OF THE INVENTION

It is the primary object of this invention to provide an ultraviolet light source which is more efficient in the desired wave length range of ultraviolet emissions than prior art devices for the polymerization of tooth restorative and sealant materials so as to cause rapid curing of such materials with a lower total power output.

It is a further object of this invention to provide a device characterized by providing efficient emission of ultraviolet light which is projected through a light transmitting and focusing means for delivery of the light to a small area in a restricted location.

It is another object of this invention to provide an ultraviolet light source which is capable of being hand-held, and which delivers an optimum amount of power at wavelengths greater than 320 nanometers.

It is a further object of this invention to provide a device for delivering ultraviolet light radiation, which device is characterized by having high efficiency emission in near ultraviolet wavelength range, and which provides a minimum amount of generated heat due to an increased operating efficiency and the elimination of emissions at unwanted wavelengths.

In accordance with the above objectives, there is provided by the present invention a light source device, having a lightweight structure suitable for hand-held operation, and having an unconfined arc xenon tube light source in operative association with light delivery means for delivering ultraviolet radiation to a restricted location, the device also having circuitry for pulsing the light source at preselected voltages and currents so as to produce a rich source of near ultraviolet light irradiance which is a function of the average power delivered to the unconfined arc xenon tube light source. The tube is operated at above 3 atmospheres pressure, optimally at about 4 atmospheres, and the irradiated energy is limited to wavelengths greater than 320 nanometers. Suitable power supplies and a pulse generator are provided in a housing which is appropriately heat sinked and is connected to the light producing source device through a coaxial transmission line to reduce to a minimum line inductance, the generated trigger pulses, so called, being connected to a trigger circuit at the light source so as to provide for delivery of a preselected number of light pulses per selected unit of time so as to maximize the average power output to correspond to wavelength emissions most desired for curing the polymerizable materials.

BRIEF DESCRIPTION OF THE DRAWINGS

FIG. 1 is a perspective view of a hand-held ultraviolet light source in combination with a power supply and pulse timing circuitry which is connected to the hand-held device through a connector.

FIG. 2 is a cross-sectional view of the portion 23 of the hand-held light source, showing the relationship of the light source to the light pipe which delivers the ultraviolet radiation.

DESCRIPTION OF THE PREFERRED EMBODIMENTS

Figure 4:
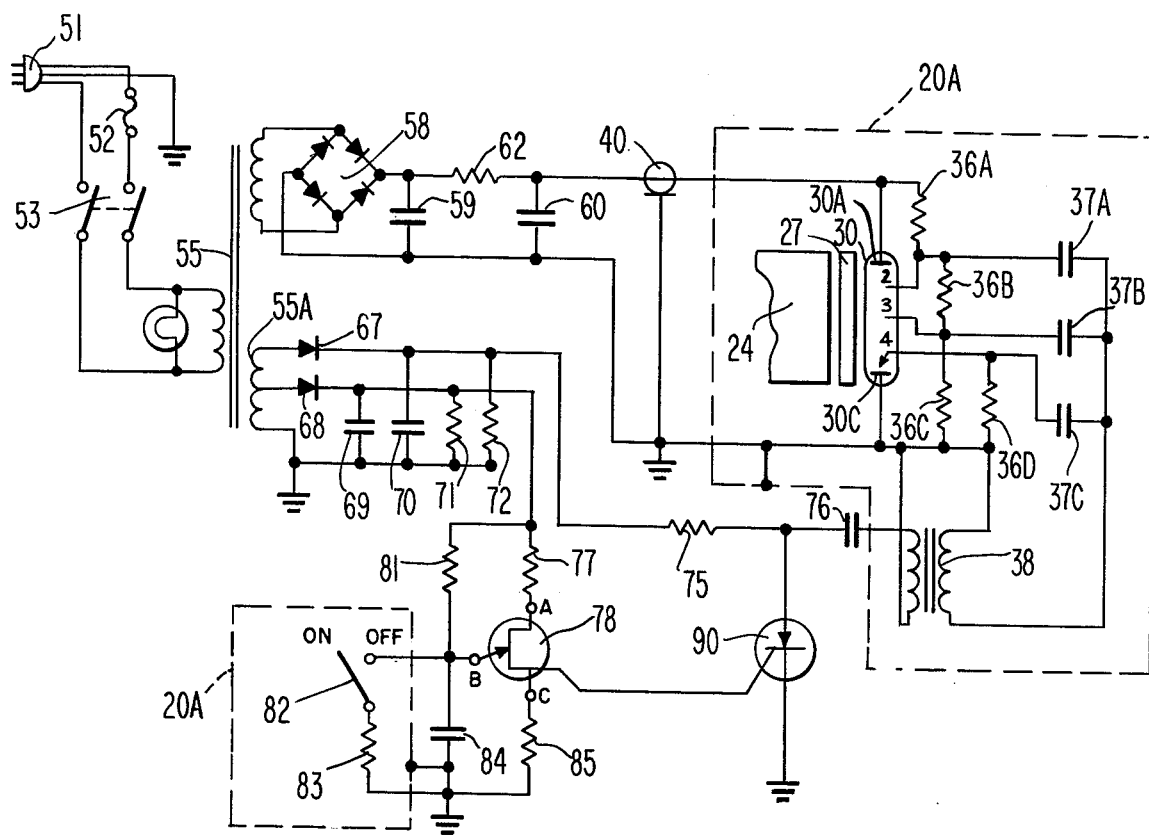
FIG. 4 is a circuit diagram of the electrical portion of a first embodiment of the light source apparatus of this invention.

Referring now to FIG. 1, the main subcomponents of the apparatus of this invention are illustrated in perspective view. A hand-held device 20, in the form of a gun, is comprised of handle 22 and the light source housing 23. Handle 22 contains a suitably located button 26 which operates electrical switch 82 shown in the schematic circuit of FIG. 4.

An ultraviolet light generating tube 30, cylindrical in geometry, is contained within the inner cylindrical surface of housing portion 23, as seen in FIG. 1 and FIG. 2. Light generating tube 30 is an unconfined xenon arc flash tube, the xenon gas pressure being maintained at a high pressure, i.e., greater than 1 atmosphere. By unconfined, it is meant that the xenon arc is not confined by a glass envelope, but rather is freely formed between the electrodes, such as the configuration of sub-atmospheric tubes manufactured by EG & G of Salem, Massachusetts. The typical lamp tube employs a number of trigger electrodes 33 (FIG. 2) for the purpose of initiating the main arc for each pulsed flash of light, which trigger electrodes help to stabilize the trigger arc and main xenon arcs with respect to position. The unconfined arc flash tube of the present invention contains a pair of closely spaced electrodes 31, anode and cathode respectively, between which the main arcs form. An unconfined arc flash tube of this configuration permits an arc as small as ⅛ inch, which is an excellent arc plasma size for directing a high percentage of the total produced light to the light rod 24 without the requirement of special reflectors and focusing devices. The envelope of tube 30 is suitably made of a glass such as CORNING 0080, which cuts off unwanted light emissions at wavelengths below 320 nanometers.

Typically, the superatmospheric unconfined arc flash tube as disclosed in this invention has the following spectral efficiency for wavelengths above 320 nm:

| WAVELENGTH | % EMISSION |
| --- | --- |
| 320 nm – 500 nm | 38.5% |
| 500 nm – 700 nm | 26.9% |
| 700 nm – 900 nm | 20.0% |
| 900 nm – 11,000 nm | 14.6% |
| 320 nm – 11,000 nm | 100% |

By contrast, the typical subatmospheric confined arc flash tube has the following spectral efficiency:

| WAVELENGTH | % EMISSION |
| --- | --- |
| 320 nm – 500 nm | 11.3% |
| 500 nm – 700 nm | 12.8% |
| 700 nm – 900 nm | 13.1% |
| 900 nm – 1100 nm | 14.7% |
| 1100 nm – 11,000 nm | 48.1% |
| 320 nm – 11,000 nm | 100% |

From the above, it is seen that the unconfined arc tube of the present invention produces a much greater output in the desired ultraviolet range (320 to 380 nm). Since the color temperatures for the superatmospheric unconfined arc tube are shifted toward the shorter wavelengths, much less tube heating is experienced (the most efficient heating wavelengths being in the 900–11,000 nm range). This low level heating is, of course, a very desirable feature for the intended dental use of the device.

The preferred gas to be used in the unconfined arc tube of this invention is xenon. The xenon tube is characterized by having a color temperature in the area of 24,000° K. and provides a substantial output continuum through the spectral range of 320 nm to 400 nm. This is in contrast to the typical prior art light source which, for example, concentrates a high percentage of its output energy in a peak at about 365 nm. It is important, for the applications discussed in the background, that the light source provide an output which is substantially continuous throughout the desired range, i.e., not have a high percentage of its output concentrated in one or several narrow peaks but have it spread out reasonably uniformly throughout the range. The xenon tube of this invention provides just such characteristic, which permits more rapid curing with a smaller energy output. For example, using the source of this invention has enabled twice as efficient a cure as a prior art device, which increased efficiency is achieved with less total emitted energy, due to the increase of produced energy between 320 nm and 380 nm.

In describing the preferred gas as xenon, it is to be noted the gas can have portions of other elements. The desired characteristic of the gas is that it have the high color temperature and substantial output continuum as described above.

In tests, it has been demonstrated that as the xenon gas pressure in the tube is increased, the level of light output increases considerably for the same electrical energy input. For example, in using this tube for curing a sealant sample of a given thickness, a time period of 10 minutes at a flash repetition rate of 60 pps was required when the xenon gas pressure was equal to atmospheric pressure. Increasing the xenon gas pressure to 3 atmospheres, while using the same repetition rate and pulse length, enabled curing of the sample of same thickness in two minutes. Other investigations have shown that with further increased pressures, additional increased ultraviolet light curing efficiency is obtained. In practice, a pressure of 4 atmospheres has been found to be optimal. The range of 3 to 10 atmospheres is desirable for operation of the device of this invention.

Specific tests have been performed on the rapid pulsed xenon device of this invention to provide data illustrative of the unique optimization obtained by operation at a gas pressure of 3 atmospheres or more. In the tests, power input to the arc tube was held constant, and ultraviolet output variations were measured as a result of variations in xenon pressure only. At 3 atmospheres, the measured output from 320 to 400 nm was equivalent to 55.49 milli-watts per sq. cm. at the contact, i.e., the tip of the light pipe. At 4 atmospheres, the measured output from 320 to 400 nm was found to be equivalent to 119.35 milli-watts per sq. cm. at the contact, representing an increase of over 100%. Controlled xenon pressure increases in increments of one atmosphere produced increases in ultraviolet output (320–400 nm) of approximately 10% except for the step from 3 to 4 atmospheres. Thus, increasing the pressure above 3 atmospheres gives an unexpected result in terms of output in the desired wavelength range. Operation around 4 atmospheres is optimum, since the resulting relatively small increases in output at greater pressures are accompanied by instability of operation. Also, at higher pressures the safety margin of the tube envelope against fracture is reduced to unacceptable levels. In summary, then, operation above 3 atmospheres provides uniquely advantageous operation for the device of this invention, where wavelengths below 320 nm are cut off, and those between 320 and 400 nm are utilized. At just 3 atmospheres, the ultraviolet power available for dental purposes (e.g., curing restorative and sealant materials) is not sufficient; at 4 atmospheres, there is available all the power that is needed to perform the curing operations in the desired time.

Figure 3:
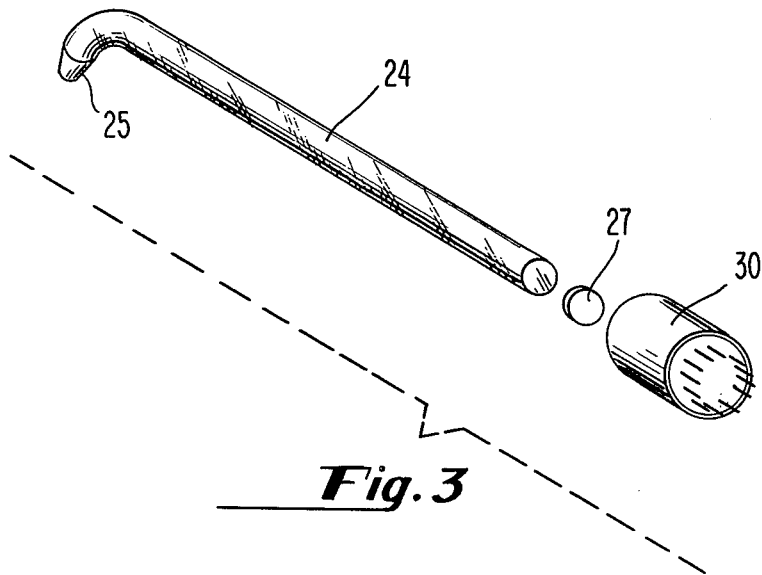
FIG. 3 is an exploded perspective view of a portion of the hand-held apparatus.

Still referring to FIGS. 1 and 2, the light pipe 24 is mounted coaxially with light housing member 23, and in operative relationship with light generating source 30, such that the main arc between electrodes 31 is positioned right in front of the inner end surface 24S of light pipe 24. In this way, there is efficient collection of the emitted ultraviolet light into pipe 24. As seen in FIG. 3, pipe 24 has a curved end, and may be adapted with a focusing piece 25 for focusing the emitted light onto the desired tooth surface. Visible light filter 27 may be placed between source 30 and pipe 24. Pipe 24 is preferably a quartz rod having an aluminized or equivalent light reflective coating thereon. Such a coating, which may be applied onto the outside of the rod by vacuum deposition, prevents light leakage at the bend or from the sides of the rod.

Most of the pulse generating circuitry is contained in housing 39 (as seen in FIG. 1), which is connected through a coaxial transmission cable 40 to the gun device 20. As explained in more detail in connection with FIG. 4, the circuitry in housing 39 provides the flash discharge energy to the lamp 30. Additionally, pulse signals are connected through a transformer 38 and a tube pulse network (made up of capacitors 37 and resistors 36) to the tube socket terminals 32. The generated trigger pulses have a fast rise time of less than about 2 microseconds, providing the starting arc that initiates the main discharge arc. Accordingly, it is desirable to have a low inductance and low resistance connection between discharge capacitor 60 and the tube discharge electrodes 30A and 30C. This is provided by use of the coaxial cable 40. It has been found that the difference between the use of an ordinary double lead connection and the coaxial lead is substantial, the coaxial lead providing a much lower circuit inductance. When the rise time of the high frequency pulses is allowed to increase due to transmission inductance, the resulting ultraviolet light energy output from the tube, when pulsed, is decreased significantly. Tests have shown that the percentage of the energy discharge through the tube during a flash, which is converted to light is about three times as great when a coaxial line is utilized.

Referring now to FIG. 4, there is shown a circuit diagram of the electrical portion of this invention. The portion of the circuitry which is contained within the dashed blocks 20A is in fact housed within the gun device 20. The remainder of the circuitry is contained in housing 39. The housing, or external portion of device 20, is electrically grounded, as shown by the connection from blocks 20A to ground.

Power is obtained through a socket 51 adapted for connection to a power line source, and fused through a conventional fuse 52. An on-off switch 53 contained on housing 39 connects the input power to transformer 55, which provides about 1400 volts across the 4 diode bridge 58, the rectified voltage being filtered by capacitor 59. The rectified and filtered voltage charges discharge capacitor 60 through resistor 62. When the tube 30 is pulsed, discharge current from capacitor 60 is transmitted through the coaxial cable to the gun device 20, where it is connected across the anode and cathode of tube 30.

The tapped secondary winding 55A provides a 20 volt source and a 200 volt source. The 20 volt DC source is provided by diode 68 connected to the winding tap, and capacitor 69 and resistor 71 connected in parallel between the cathode of diode 68 and ground. This 20 volt supply is connected through resistor 77 to terminal A of unijunction transistor 78. Terminal C is connected through resistor 85 to ground. Terminal B of transistor 78 is connected to the 20 volt supply through resistor 81, and to ground through capacitor 84. Terminal B is also connected through on-off switch 82 (operated by the switch designated 26 in FIG. 1) through resistor 83 to ground. When switch 82 is in the position shown as "on", unijunction transistor 78 and its associated circuitry comprise a pulse generator producing rapid rise pulses at the rate of about 60 pulses per second, the frequency being established by the values of 81 and 84. It is understood that this pulse repetition rate could be varied from 60 pps, which is an illustrative figure.

The 200 volt source is derived from the transformer winding 55A through the half wave rectifier 67, filtered by capacitor 70, across which discharge resistor 72 is connected to ground. This source supplies 200 volts through charging resistor 75 to capacitor 76 and the anode of SCR 90. The output of the pulse generator is taken from terminal C to the gate of SCR 90. The cathode of SCR 90 is connected to ground. The SCR 90 is switched on and off 60 times per second, discharging capacitor 76 into the primary winding of transformer 38. The pulses delivered at the secondary of transformer 38 are in the order of 5000 volts, and are delivered through a trigger network comprising capacitors 37A, 37B and 37C in combination with resistors 36A, 36B, 36C, and 36D. As seen in the illustration of FIG. 4, the trigger pulses are applied in parallel to trigger probes 2, 3 and 4 spaced between the anode 30A and cathode 30C of tube 30. A small streamer arc is formed from 30C to 4, then to 3, then to 2 and on to 30A, such that the streamer arc is constructed between 30C and 30A. Capacitor 60 then discharges, forming the main light producing arc. Once the discharge is completed, the main arc turns off, capacitor 60 re-charges, and the tube flashes again when the next trigger pulse arc is formed.

In practice, it has been found that the method of pulsing the unconfined arc high pressure tube, as disclosed herein, produces a high efficiency emission of near ultraviolet light energy for deliverance to the tooth surface. By maintaining the tube at a superatmospheric, or high pressure, preferably at least 3 atmospheres, there is no need to include after fire inhibitors within the xenon flash tube, which inhibitors reduce ultraviolet light output. This aids in providing a high efficiency emission in the near ultraviolet wavelength range.

Figures 5, 6:
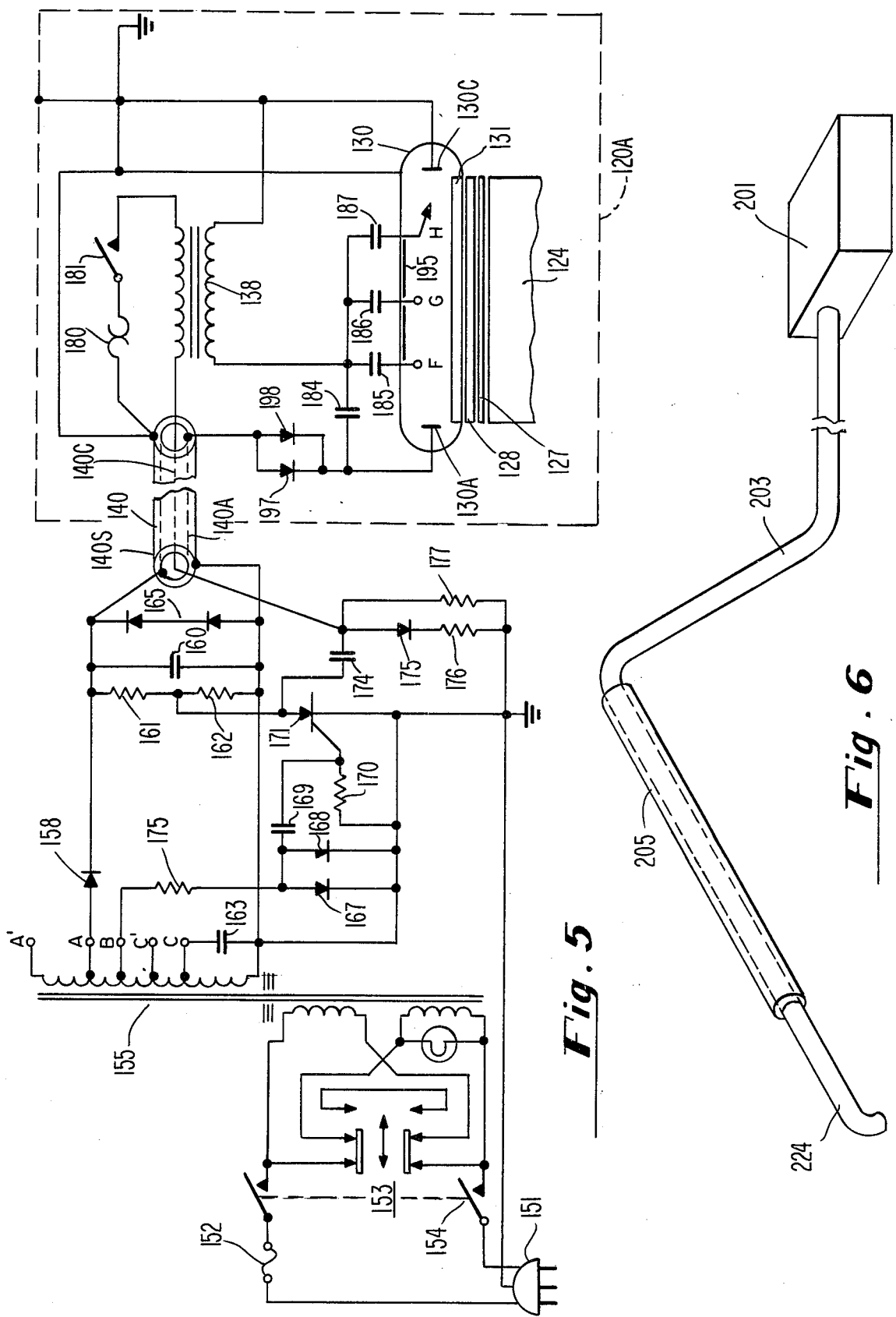
FIG. 5 is a circuit diagram of a second embodiment of the light source apparatus of this invention.
FIG. 6 is a schematic representation of a system using the light source apparatus of this invention and employing a light pipe between the ultraviolet source and the hand-held gun.

Referring now to FIG. 5, there is shown a modified form of a circuit arrangement for triggering and pulsing the ultraviolet light source of this invention. The second two digits of the numeral designations of this circuit are the same, where applicable, as the corresponding digits of similar components in FIG. 4. This circuit utilizes a constant voltage transformer 155, preferably a ferroresonant constant voltage transformer. The incorporation of such a transformer makes allowance automatically for power line voltage variations, which usually fall within $^{+15\%}_{-30\%}$ of the nominal line voltage. A constant voltage transformer corrects within ±1% on the secondary side of the transformer. Such correction is highly desirable to enable the light source to operate efficiently at a low power level, thus extending the life of the tube. The dashed block 120A indicates that portion of the circuitry and apparatus which is contained within the handpiece 20.

Still referring to FIG. 5, the power input is obtained through plug 151, one line of which is grounded and one line of which is connected through fuse 152. A third line is connected through on-off switch 154 to switch 153, which latter switch is utilized to set the apparatus for either 115 volt or 230 volt operation. The output of switch 153 is connected to the input primary windings of constant voltage transformer 155. The secondary of transformer 155 has various terminals for connection depending upon whether the local power source is 115 volt 60 Hz, or 230 volt 50 Hz. The discharge capacitor 160 is charged from secondary terminal A (or A') through diode 158 every positive swing of the power line. Resistors 161 and 162 form a voltage divider, and a connection is made between such resistors to the anode of SCR 171 as well as to capacitor 174, such that capacitor 174 is charged at the same time that the discharge capacitor is charged. The trigger circuit voltage is derived from terminal B of the secondary of transformer 155. Terminal B is connected through resistor 175 to diode 167 and hybrid diode 168, which are also connected through capacitor 169 to the gate of SCR 171. The gate is connected through low value resistor 170 to ground. Resonant capacitor 163 is connected between ground and either terminal C or C', depending upon whether the power source is 50 Hz or 60 Hz.

In this embodiment, a triaxial cable 140 is utilized. Discharge capacitor 160 is connected to two of the conductors of cable 140, namely 140A and 140S. Two diodes 165 are connected in series across main discharge capacitor 160, which in combination with the high voltage surge diodes 197 and 198 assure that proper polarity of the triggering sequence across the tube 130 is achieved. A damping network comprised of diode 175 in series with resistor 176, and resistor 177, which network is connected between capacitor 174 and ground, serves to dampen the ringing effect caused by the inductance of transformer 138 at the time that a trigger pulse is transmitted. As is developed hereinbelow, the trigger pulse is taken from the junction between capacitor 174 and diode 175, and connected to the center conductor 140C of the triaxial cable, the other end of which is connected to the primary of transformer 138 which suitably has a 15:1 ratio.

At the UV tube 130, the output of transformer 138 is connected across the tube anode 130A through capacitor 184 and the tube cathode 130C. The transformer output is also connected through the capacitor network comprising capacitors 184, 185, 186 and 187 to the trigger electrodes F, G and H.

The following represent typical values and designations of components of the circuit of FIG. 5:

| | |
|---|---|
| Diode 158 | 2.5 Kv piv, 500 ma Avg. |
| Capacitor 160 | 2µf |
| Resistor 161 | 470 Kohm |
| Resistor 162 | 470 Kohm |
| Diodes 165 | IN 4725 |
| Diode 167 | IN914 |
| Hybrid Diode 168 | IN5758 |
| Capacitor 169 | .022µf |
| Resistor 170 | 100 ohm |
| SCR 171 | RCA 52600M |

-continued

| | |
|---|---|
| Capacitor 174 | .01µf |
| Diode 175 | IN4005 |
| Resistor 176 | 51 ohm |
| Resistor 177 | 1 Kohm |
| Capacitors 184 – 187 | 22pf |

In the operation of this circuit, trigger pulses are generated at the power line frequency. The main discharge capacitor is charged to a full charge during the positive half of the cycle and is triggered to discharge during the negative half of the cycle. This method of charging and discharging energy into the tube accomplishes stable tube pulsing without the need for a charging resistor, thus providing good power supply efficiency and fewer circuit components. During the positive half cycle when main discharge capacitor 160 is charging, trigger capacitor 174 is charging through resistor 161. During this time, diode 167 conducts and prevents capacitor 169 from charging. During the negative half cycle of the power line, capacitor 169 charges through resistor 175. When it charges to a value of about 20 volts, it discharges through diode 168 which conducts when such a back voltage is placed across it. This discharge generates a signal across resistor 170 which gates on SCR 171, which then provides a discharge path for capacitor 174. The rapid discharge of capacitor 174 produces the trigger pulse which is transmitted through the triaxial cable conductor 140C and transformer 138 to trigger the tube 130. As stated previously, the damping circuit dampens any ringing effect caused by the inductance of transformer 138, so that only a single trigger pulse is transmitted through to the tube. The trigger pulse causes formation of a trigger arc in the tube, following which the energy stored in the main discharge capacitor 160 is discharged in the main arc through the tube.

The tube 130, as utilized in the embodiment of FIG. 5, is comprised of a tube envelope which is opaque to the emissions of the discharge, suitably of stainless steel and preferably non-oxidizing. The tube utilizes a relatively small (15 mm diameter) glass window 131 through which the ultraviolet light is transmitted. This window is made of a glass which cuts off wavelengths below 320 mn. Additionally, for extra security against unwanted radiation, one or more sharp cut off light filters 128 may be positioned adjacent window 131, and suitably cemented to visible light filter 127. Filter 128 may, for example, cut off wavelengths less than 320 nm, less than 325 nm, less than 330 nm, etc., as desired. Also, a reflector as shown diagrammatically at 195, or reflectors, may be positioned inside the tube and opposite from window 131, to optimize transmission of the ultraviolet radiation out of the window and into the light pipe.

Testing with the apparatus of this invention has led to the conclusion that the visible light filter 127 is highly desirable. The intensity of the visible light which is otherwise transmitted through to the tube surface and reflected therefrom can cause considerable operator eye fatigue. It is to be noted that the glass in the window 131 cuts off the harmful shorter wavelengths, while the visible light filter serves the function of eliminating visible light which would otherwise cause operator eye fatigue. The visible light filter must, of course, have a bandpass characteristic at the desired UV wavelength, between 320 and 380 nanometers. The commercially available glass filter 127 which has been used with this apparatus reduces the visible light to about 5%, while introducing approximately only 8% loss at the desired UV wavelength. By maintaining about 5% of the visible light, there is sufficient projection onto the tooth surface to aid the user in aiming the gun output.

The two embodiments which have been described hereinabove provide a UV source for dental application with greatly improved safety features. The UV gun of this invention utilizes a quartz rod 24 (or 124), which is an excellent electrical insulator, and which is mounted into a handpiece which is grounded back to chassis ground. Through the use of the quartz rod any high voltage is kept from entering the oral cavity of the patient. Further, by utilizing the optical window 131 of CORNING 0800 glass, which absorbs the short ultraviolet wavelengths below the desired wavelength range, an additional substantial safety increase is achieved. The design is fail safe, in that if the window cracks, the gas escapes and the tube becomes inoperative. By contrast, in apparatus which depends solely upon an external filter, if the filter cracks harmful radiation is emitted, and there is no way to discern the dangerous condition of the apparatus. Thermo-switch 180 protects the handpiece configuration from exceeding a predetermined temperature, it automatically shuts off until it cools down to a given lower temperature.

The optical window 131 is fused to the inside of the metal envelope opening, which construction further prevents short wavelength ultraviolet leakage. This arrangement has produced a reliable UV source which operates at an average power of 70 watts to derive the level of UV output required for curing the restorative and sealant materials within a time period of approximately one-half the cure time of prior art systems. The rapid pulse light apparatus of this invention also provides a source which requires substantially no warm-up time. The apparatus requires approximately 1.0 ms for full light output when the power line switch and trigger switch are turned on at the same time.

Referring now to FIG. 6, there is shown a diagrammatic view of another embodiment of this invention. In this embodiment, the power supply and all of the electronic circuitry are housed in an external housing 201, along with the ultraviolet source, i.e., the tube and associated trigger circuit components. Thus, in this embodiment, the ultraviolet light pulses are generated externally to the actual hand-held device which delivers the curing ultraviolet light pulses to the tooth surface. Connecting between housing 201 and the hand-held delivery means 205 is a light pipe, or light guide 203. Such light guides or light pipes are commercially available, and are generally of either the fiber-optic type or the liquid filled pipe type. In this arrangement, the handpiece 205 can be very small, and in fact pencil-like in size. There are no heat problems associated with the handpiece itself, since it is acting as simply a conduit for the light which is generated at an external point. Of course, the output of the source within housing 201 is, in this embodiment, adjusted to take into account any attenuation of the light as it is transmitted through the pipe 203 to the handpiece. Also, wavelength band pass characteristics between 320 nm and 380 nm must be taken into consideration in optimizing a particular light guide design. The liquid filled light guides can be made to be wavelength or band pass selective, which eliminates the need for the visible light filter 128, as shown in FIG. 5. Appropriate changes in the power supply voltage and other circuit parameters are a matter of design choice, and within the state of the art.

The ultraviolet source apparatus as described possesses unique advantages over any prior art device for efficiently producing power in the range of 320 to 380 nm. As soon as the pressure of the xenon is raised from 3 atmospheres, a substantial increase is achieved in power delivered within such range; since the largest increase is observed up to and around 4 atmospheres, the optimum design of the apparatus of this invention calls for the pressure to be greater than 3 and up to around 4 atmospheres. However, increased power in the desired range is observed up to a pressure of 10 atmospheres. As stated previously, for the apparatus disclosed, operation at the higher pressures is likely to be less stable, and the disclosed glass window is in greater danger of fracture. However, a stronger window (having the same cut-off characteristic) may be utilized, and the device may be usefully employed at the higher pressures for applications where greater power in the 320–380 nm range is necessary.

I claim:

1. Light source apparatus for delivering a substantial continuum of ultraviolet radiation in the range of 320 to 400 nanometers to a restricted surface area, comprising:
   a. ultraviolet light source means containing xenon at greater than 3 atmospheres and less than 10 atmospheres pressure, and including means to cut off wavelengths below 320 nanometers;
   b. a housing, adapted to contain said ultraviolet light source means and suitable for hand-held operation;
   c. means for pulsing of said ultraviolet light source means; and
   d. light delivery means in operative association with said light source means for delivering ultraviolet radiation from said light source means to the restricted surface area.

2. The apparatus as described in claim 1, wherein said light source means comprises an unconfined arc tube which contains xenon gas maintained at said pressure.

3. The apparatus as described in claim 2, wherein said pressure is in the range of greater than 3 and less than 10 atmospheres.

4. The apparatus as described in claim 2, wherein said xenon pressure is about 4 atmospheres.

5. The apparatus as described in claim 2, wherein said cutoff means comprises an envelope portion of said tube which blocks transmission from said tube of wavelengths less than 320 nanometers.

6. The apparatus as described in claim 5, wherein said envelope portion comprises a glass window having glass which cuts off light wavelengths shorter than 320 nanometers and passes wavelengths greater than 320 nanometers.

7. The apparatus as described in claim 2, containing a power supply for delivering electrical power for said light source tube and trigger pulse circuitry for delivering trigger pulses to said light source tube, said power supply and trigger pulse circuitry being contained in a second housing outside of said housing, and coaxial connecting means between said outside housing and said light source tube for delivery of said electrical power and trigger pulses.

8. The apparatus as described in claim 1, wherein said pulsing means comprises means for high rate rapid pulsing of said light source means.

9. The apparatus as described in claim 8, wherein said means for high rate rapid pulsing of said light source delivers trigger pulses with a rise time of less than about 2 microseconds, and at a pulse repetition rate of at least about 100 per second.

10. Light source apparatus for providing efficient emission of ultraviolet radiation, comprising:
   a. an unconfined xenon arc tube, said tube having an anode and a cathode and a plurality of trigger electrodes, said tube further having a glass window with a cut-off characteristic which prevents radiation from said tube at wavelengths below 320 nanometers, and being maintained at a pressure of at least 3 and less than 10 atmospheres; and
   b. triggering and power means for delivering at a high rate rapid rise trigger pulses to said trigger electrodes, and for delivering power to said tube, said tube producing ultraviolet radiation upon being triggered by said trigger pulses.

11. The light source apparatus as described in claim 10, wherein said light source means is housed within a housing suitable for hand-held operation, and having means for directing the ultraviolet light at a restricted surface area.

12. The apparatus as described in claim 10, comprising:
   a. external housing for containing said light source apparatus;
   b. hand-held means for directing ultraviolet light at a restricted surface area; and
   c. light guide means for transmitting said produced ultraviolet radiation from said external housing to said hand-held means.

13. The apparatus as described in claim 10, wherein said tube is enclosed by a housing which is opaque to the radiation produced by said tube, said housing having an opening within which is sealed said window.

14. The apparatus as described in claim 13, comprising a light delivery means for delivering said ultraviolet radiation, and a visible light filter positioned between said window and said light delivery means.

* * * * *